US006168628B1

(12) United States Patent
Huebner

(10) Patent No.: US 6,168,628 B1
(45) Date of Patent: Jan. 2, 2001

(54) SHOULDER PROSTHESIS

(75) Inventor: Randall J. Huebner, Beaverton, OR (US)

(73) Assignee: Acumed, Inc., Beaverton, OR (US)

( * ) Notice: Under 35 U.S.C. 154(b), the term of this patent shall be extended for 0 days.

(21) Appl. No.: 09/484,339

(22) Filed: Jan. 18, 2000

Related U.S. Application Data

(63) Continuation of application No. 09/191,928, filed on Nov. 13, 1998, which is a continuation-in-part of application No. 09/040,504, filed on Mar. 17, 1998, now Pat. No. 5,961,555, and a continuation-in-part of application No. 09/165,475, filed on Oct. 2, 1998.

(51) Int. Cl.[7] .............................. A61F 2/40; A61B 17/56
(52) U.S. Cl. .......................................... 623/19.11; 606/86
(58) Field of Search ............................. 623/19.11, 19.12, 623/19.13, 19.14, 20.14; 606/62, 64, 96, 98, 104, 86, 87

(56) References Cited

U.S. PATENT DOCUMENTS

| 2,682,265 | 6/1954 | Collison . |
| 2,719,522 | 10/1955 | Hudack . |
| 2,765,787 | 10/1956 | Pellet . |
| 2,781,758 | 2/1957 | Chevalier . |
| 2,785,673 | 3/1957 | Anderson . |
| 3,064,645 | 11/1962 | Ficat et al. . |
| 3,067,740 | 12/1962 | Haboush . |
| 3,102,536 | 9/1963 | Rose et al. . |
| 3,658,056 | 4/1972 | Huggler et al. . |
| 3,670,724 | 6/1972 | Bosacco . |
| 3,694,820 | 10/1972 | Scales et al. . |
| 3,782,373 | 1/1974 | Smythe . |
| 3,806,957 | 4/1974 | Shersher . |
| 3,814,089 | 6/1974 | Deyerle . |
| 3,818,512 | 6/1974 | Shersher . |
| 3,859,669 | 1/1975 | Shersher . |
| 3,863,273 | 2/1975 | Averill . |
| 3,874,003 | 4/1975 | Moser et al. . |

(List continued on next page.)

FOREIGN PATENT DOCUMENTS

| 2015324 | 11/1971 | (DE) . |
| 2400650 | 7/1974 | (DE) . |
| 3023354A1 | 4/1981 | (DE) . |
| 3329978A1 | 3/1985 | (DE) . |
| 3415934A1 | 10/1985 | (DE) . |
| 4320086C2 | 10/1995 | (DE) . |
| 19548154A1 | 6/1997 | (DE) . |

(List continued on next page.)

OTHER PUBLICATIONS

Capanna et al., "A Humeral Modular Prostheses for Bone Tumour Surgery: A Study of 56 Cases," *International Orthopaedics*, vol. 10, No. 4, pp. 231–238, 1986.
The BiAngular Shoulder brochure, Biomet, Inc., ©1989.
Bio–Modular Total Shoulder brochure, Biomet, Inc., ©1990.
Robert et al., "The Geometry of the Humeral Head and the Design of Prosthesis," *The Journal of Bone and Joint Surgery*, vol 73–B, No. 4, Jul. 1991.
Buechel–Pappas Total Shoulder System instructions, Oct. 1991.

(List continued on next page.)

*Primary Examiner*—David J. Isabella
(74) *Attorney, Agent, or Firm*—Kolisch, Hartwell, Dickinson, McCormack & Heuser

(57) ABSTRACT

A shoulder prosthesis having a head and an elongate stem portion including a proximal end connected to the head, a distal section for insertion into a medullary canal of a humeral bone and an alignment section disposed between the proximal end and distal section. The alignment section includes a plurality of reference marks positioned to facilitate placement of the prosthesis in the bone at a previously determined position.

16 Claims, 11 Drawing Sheets

U.S. PATENT DOCUMENTS

| | | |
|---|---|---|
| 3,906,550 | 9/1975 | Rostoker et al. . |
| 3,916,451 | 11/1975 | Buechel et al. . |
| 3,918,441 | 11/1975 | Getscher . |
| 3,974,527 | 8/1976 | Shersher . |
| 3,979,778 | 9/1976 | Stroot . |
| 3,987,499 | 10/1976 | Scharbach et al. . |
| 4,004,300 | 1/1977 | English . |
| 4,030,143 | 6/1977 | Elloy et al. . |
| 4,040,131 | 8/1977 | Gristina . |
| 4,042,980 | 8/1977 | Swanson et al. . |
| 4,051,559 | 10/1977 | Pifferi . |
| 4,115,875 | 9/1978 | Rambert et al. . |
| 4,261,062 | 4/1981 | Amstutz et al. . |
| 4,404,691 | 9/1983 | Buning et al. . |
| 4,406,023 | 9/1983 | Harris . |
| 4,430,761 | 2/1984 | Niederer et al. . |
| 4,459,708 | 7/1984 | Buttazzoni . |
| 4,488,319 | 12/1984 | von Recum . |
| 4,532,660 | 8/1985 | Field . |
| 4,550,450 | 11/1985 | Kinnett . |
| 4,578,081 | 3/1986 | Harder et al. . |
| 4,624,674 | 11/1986 | Pappas et al. . |
| 4,645,506 | 2/1987 | Link . |
| 4,655,778 | 4/1987 | Koeneman . |
| 4,676,797 | 6/1987 | Anapliotis et al. . |
| 4,693,723 | 9/1987 | Gabard . |
| 4,693,724 | 9/1987 | Rhenter et al. . |
| 4,698,063 | 10/1987 | Link et al. . |
| 4,822,370 | 4/1989 | Schelhas . |
| 4,840,632 | 6/1989 | Kampner . |
| 4,842,606 | 6/1989 | Kranz et al. . |
| 4,865,605 | 9/1989 | Dines et al. . |
| 4,865,609 | 9/1989 | Roche . |
| 4,893,619 * | 1/1990 | Dale et al. ............................ 606/87 |
| 4,895,572 | 1/1990 | Chernoff . |
| 4,904,266 | 2/1990 | Barber . |
| 4,908,032 | 3/1990 | Keller . |
| 4,919,669 | 4/1990 | Lannelongue . |
| 4,919,670 | 4/1990 | Dale et al. . |
| 4,932,974 | 6/1990 | Pappas et al. . |
| 4,959,066 * | 9/1990 | Dunn et al. ............................ 606/87 |
| 4,963,155 | 10/1990 | Lazzeri et al. . |
| 4,986,833 | 1/1991 | Worland . |
| 4,995,883 | 2/1991 | Demane et al. . |
| 5,002,580 | 3/1991 | Noble et al. . |
| 5,002,581 | 3/1991 | Paxson et al. . |
| 5,030,234 | 7/1991 | Pappas et al. . |
| 5,032,130 | 7/1991 | Schelhas et al. . |
| 5,074,879 | 12/1991 | Pappas et al. . |
| 5,080,676 | 1/1992 | May . |
| 5,080,685 | 1/1992 | Bolesky et al. . |
| 5,108,437 | 4/1992 | Kenna . |
| 5,108,452 | 4/1992 | Fallin . |
| 5,116,379 | 5/1992 | McLardy-Smith . |
| 5,135,529 | 8/1992 | Paxson et al. . |
| 5,169,401 | 12/1992 | Lester et al. . |
| 5,181,928 | 1/1993 | Bolesky et al. . |
| 5,207,682 * | 5/1993 | Cripe ............................ 606/96 |
| 5,261,915 | 11/1993 | Durlacher et al. . |
| 5,282,865 | 2/1994 | Dong . |
| 5,286,260 | 2/1994 | Bolesky et al. . |
| 5,314,479 | 5/1994 | Rockwood, Jr. et al. . |
| 5,336,268 | 8/1994 | Rispeter . |
| 5,342,363 | 8/1994 | Richelsoph . |
| 5,342,366 * | 8/1994 | Whiteside et al. ............ 606/86 |
| 5,358,526 | 10/1994 | Tornier . |
| 5,370,706 | 12/1994 | Bolesky et al. . |
| 5,405,403 | 4/1995 | Mikhail . |
| 5,433,720 * | 7/1995 | Faccioli et al. ............... 606/87 |
| 5,489,309 | 2/1996 | Lackey et al. . |
| 5,507,817 | 4/1996 | Craig et al. . |
| 5,507,818 | 4/1996 | McLaughlin . |
| 5,514,143 * | 5/1996 | Bonutti et al. ............... 606/86 |
| 5,549,682 | 8/1996 | Roy . |
| 5,580,352 | 12/1996 | Sekel . |
| 5,591,233 | 1/1997 | Kelman et al. . |
| 5,645,548 | 7/1997 | Augsburger . |
| 5,645,607 | 7/1997 | Hickey . |
| 5,649,930 * | 7/1997 | Kertzner ....................... 606/96 |
| 5,658,340 | 8/1997 | Muller et al. . |
| 5,662,651 | 9/1997 | Tornier et al. . |
| 5,702,447 | 12/1997 | Walch et al. . |
| 5,702,457 | 12/1997 | Walch et al. . |
| 5,779,709 | 7/1998 | Harris, Jr. et al. . |
| 5,788,700 | 8/1998 | Morawa et al. . |
| 5,800,560 | 9/1998 | Draenert . |

FOREIGN PATENT DOCUMENTS

| | | |
|---|---|---|
| 0000549A1 | 2/1979 | (EP) . |
| 0017743A1 | 10/1980 | (EP) . |
| 0098224A1 | 1/1984 | (EP) . |
| 0145939A2 | 8/1985 | (EP) . |
| 0163121A1 | 12/1985 | (EP) . |
| 0190981A1 | 8/1986 | (EP) . |
| 0198163A2 | 10/1986 | (EP) . |
| 0201407A1 | 11/1986 | (EP) . |
| 0243298A2 | 10/1987 | (EP) . |
| 0278807A2 | 8/1988 | (EP) . |
| 0339530A2 | 2/1989 | (EP) . |
| 0393608A2 | 10/1990 | (EP) . |
| 0501207A1 | 9/1992 | (EP) . |
| 0611225A1 | 8/1994 | (EP) . |
| 0617934A1 | 10/1994 | (EP) . |
| 0622062A1 | 11/1994 | (EP) . |
| 0634154A1 | 1/1995 | (EP) . |
| 0639359A1 | 2/1995 | (EP) . |
| 0679375A1 | 11/1995 | (EP) . |
| 0715836A1 | 6/1996 | (EP) . |
| 0679375B1 | 9/1998 | (EP) . |
| 2225141 | 4/1974 | (FR) . |
| 2378505 | 8/1978 | (FR) . |
| 2567019 | 1/1986 | (FR) . |
| 2574283 | 6/1986 | (FR) . |
| 2576793 | 8/1986 | (FR) . |
| 2579454 | 10/1986 | (FR) . |
| 2606273 | 5/1988 | (FR) . |
| 2619502 | 2/1989 | (FR) . |
| 2634371 | 1/1990 | (FR) . |
| 2652498 | 4/1991 | (FR) . |
| 2664809 | 1/1992 | (FR) . |
| 2670108 | 6/1992 | (FR) . |
| 2689756 | 10/1993 | (FR) . |
| 2689757 | 10/1993 | (FR) . |
| 2689758 | 10/1993 | (FR) . |
| 2699400 | 6/1994 | (FR) . |
| 2705558 | 12/1994 | (FR) . |
| 2737107 | 1/1997 | (FR) . |
| 1443470 | 7/1976 | (GB) . |
| 1521679 | 8/1978 | (GB) . |
| 1531487 | 11/1978 | (GB) . |
| 2070939 | 9/1981 | (GB) . |
| 2223172 | 4/1990 | (GB) . |
| 1279629A1 | 12/1986 | (SU) . |
| WO83/02555 | 8/1983 | (WO) . |
| WO91/18559 | 12/1991 | (WO) . |
| WO94/15551 | 7/1994 | (WO) . |
| WO96/17553 | 6/1996 | (WO) . |
| WO96/41597 | 12/1996 | (WO) . |
| WO98/46172 | 10/1998 | (WO) . |

OTHER PUBLICATIONS

Moeckel et al., "Modular Hemiarthroplasty for Fractures of the Proximal Part of the Humerus," *The Journal of Bone and Joint Surgery, Inc.*, vol. 74–A, No. 6, pp. 884–889, Jul. 1992.

Iannotti et al., "Total Shoulder Arthroplast: Factors Influencing Prosthetic Sizing," *University of Pennsylvania Medical Center*, 1994.

Fenlin, Jr. et al., "Modular Total Shoulder Replacement: Design Rationale, Indications, and Results," *Clinical Orthopaedics and Related Research*, No. 307, pp. 37–46, ©1994.

Pearl et al., "Retroversion of the Proximal Humerus in Relationship to Prosthetic Replacement Arthroplasty," *J. Shoulder Elbow Surg.*, vol. 4, No. 4, Jul./Aug. 1995.

Romeo, "Total Shoulder Arthroplasty: Pearls and Pitfalls in Surgical Technique," *Seminars in Arthroplasty*, vol. 6, No. 4, Oct. 1995.

Global Total Shoulder Arthroplasty System brochure, 1995.

Four Part Humeral Fracture Repair description, DePuy, Inc., 1995.

The Neer II Total Shoulder System, The 3M™Modular Shoulder System brochure, Wright Medical Technology, Inc., ©1995.

Fenlin Total Shoulder brochure, Zimmer, Inc., ©1998.

Intermedics Orthopedics Select Shoulder System, Intermedics Orthopedics, Inc., undated.

Shoulder Prosthesis description, Tornier, undated.

The Aequalis Shoulder Prosthesis brochure, Tornier, Inc., undated.

\* cited by examiner

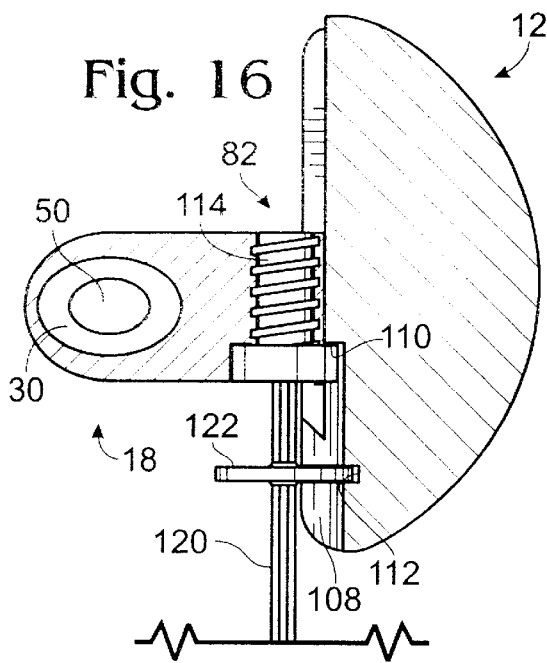
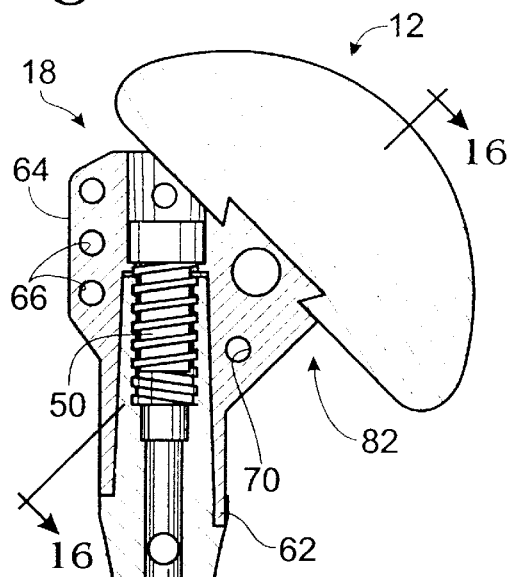
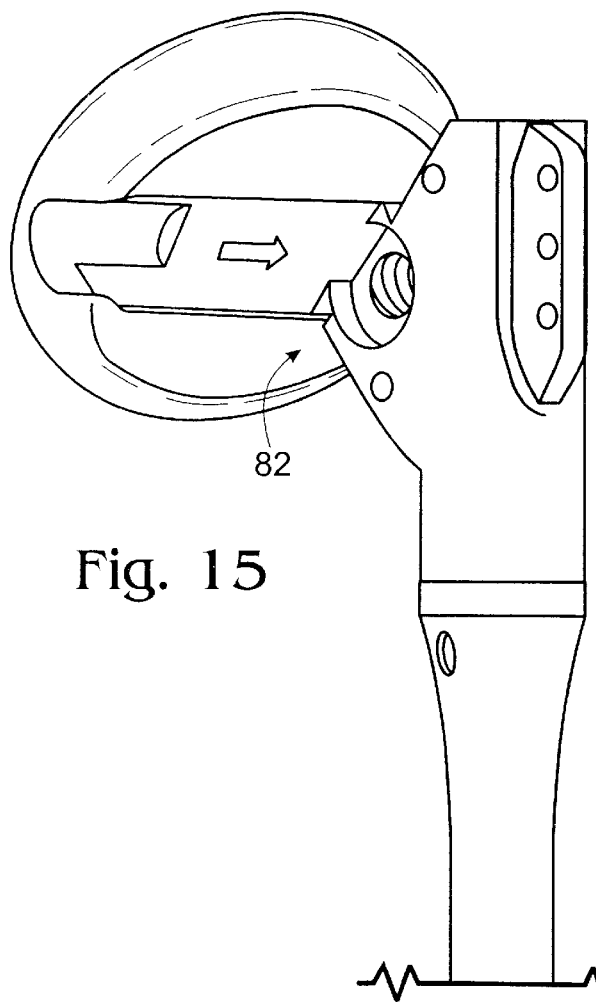

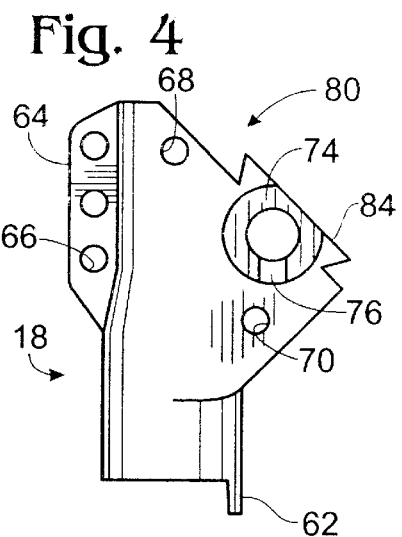
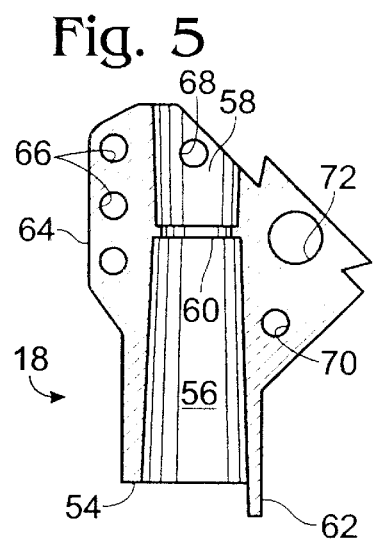
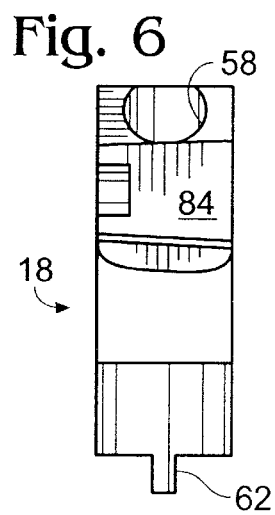
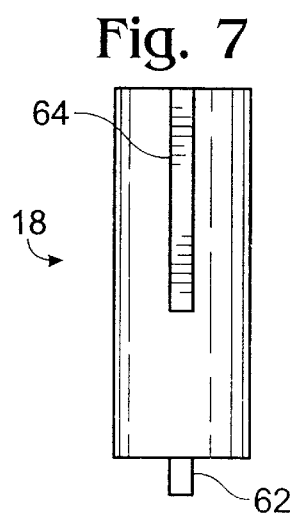
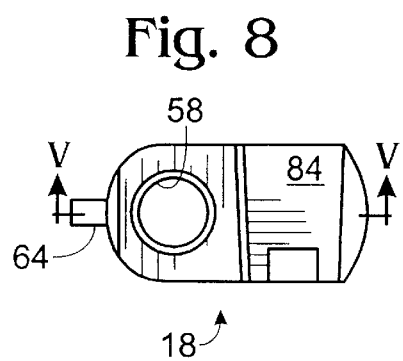
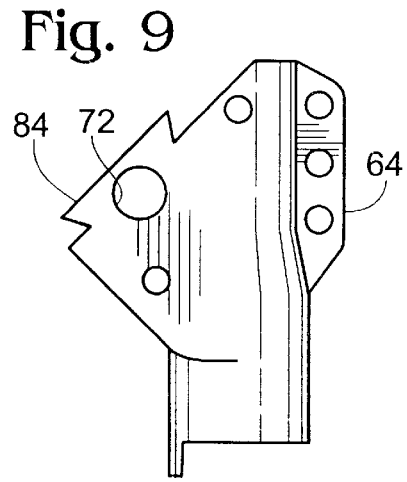

SHOULDER PROSTHESIS

CROSS-REFERENCE TO RELATED APPLICATIONS

This application is a continuation of U.S. patent application Ser. No. 09/191,928, filed Nov. 13, 1998, which is a continuation-in-part of U.S. patent application Ser. No. 09/040,504, filed Mar. 17, 1998, issued as U.S. Pat. No. 5,961,555 on Oct. 5, 1999, and U.S. patent application Ser. No. 09/165,475, filed Oct. 2, 1998.

This invention relates generally to bone prostheses and more particularly to a shoulder prosthesis.

BACKGROUND OF THE INVENTION

When a joint, such as the hip or shoulder, becomes impaired due to arthritis, disease or trauma, it is sometimes necessary to replace all or part of the joint with a prosthesis to restore function. For instance, hip replacement, where a prosthesis is provided to replace the femoral head and in some cases all or part of the acetabulum, has become a common procedure to treat femoral head fractures and arthritis in elderly patients. As a result of anatomical constraints and challenges in the shoulder, shoulder implants have historically been much less successful and less common than hip replacements. Recently, however, shoulder arthroplasty has emerged as an accepted treatment for severe arthritis and humeral head fractures.

As a consequence of the increasing acceptance of shoulder prostheses, many different devices have been developed to address various problems that have arisen and to offer additional benefits and features. In the simplest form, a shoulder prosthesis is formed as a single piece with a head to articulate with the glenoid cavity, and a stem to extend down the medullary canal of the humerus and support the head. While simple to construct, unitary implants do not offer any adjustability to accommodate the natural variations in size and geometry that occur among joints of different patients. To accommodate these variations, a large stock of devices must be manufactured and maintained to insure that an adequate match can be achieved during an operation. Stocking the large number of devices is a significant expense with one-piece designs, and in some cases a surgeon may not be provided with sufficient flexibility to achieve an ideal fit to the patient.

To avoid the expense of maintaining a large stock of single-piece prosthetics and to provide increased flexibility to surgeons, many shoulder implant makers have gone to a modular design that is assembled during the operation from two or three pieces. These pieces include a head to articulate with the glenoid and a stem structure on which the head is mounted and secured to the bone. In some cases, the stem includes a separate body portion disposed between the head and an intermedullary portion of the stem that extends down the medullary canal. By utilizing a modular design, a wide variety of devices can be assembled from only a few pieces, thus providing increased flexibility to accommodate anatomical variation and eliminating much of the cost associated with maintaining a large selection of one-piece devices.

Existing modular shoulder designs most commonly rely on a taper lock mechanism to secure the head to the rest of the implant. In at least some devices the portion of the taper lock on the head is offset to compensate for anatomical posterior offset of the humeral head. For instance, the taper lock portion on the head may be offset by 2–4 millimeters. By rotating the head, any offset between plus and minus the 2–4 millimeters can be achieved. Unfortunately, rotating an offset head can introduce a medial/lateral and/or superior/inferior offset at the same time the anterior/posterior positioning is adjusted. Furthermore, the offset between the center of the taper lock and the geometrical center of the head creates a torque which tends to rotate the head relative to the remainder of the implant, thereby increasing the chance of loosening of the head. As the offset increases, the resultant torque increases as well, making this a greater problem for larger offsets. Although such problems are incumbent in existing offset head designs, a posterior offset is generally desirable to better match the natural anatomy.

In addition to the specific drawbacks associated with various existing implant designs, there are a number of general problems inherent in shoulder replacements. In particular, it is generally difficult to establish the proper position and orientation for the implant in the humerus. One of the more important variables is the rotational position, or retroversion, of the head on the humerus. Anatomically, the average retroversion between a plane defined by the perimeter of the anatomical head and the axis of the flexed forearm is approximately 30-degrees. Unfortunately, with existing implants and techniques for their installation, it has been very difficult to reliably reproduce desired retroversion. Establishing correct retroversion is important because incorrect retroversion can lead to problems with subsequent dislocation.

In addition to the retroversion of the implant, it is necessary to establish the correct height of the implant on the humeral shaft. With existing designs, the surgeon slips the stem into the medullary canal and makes an educated guess at the proper height. Excess height may create too much tension in the deltoid, while inserting the implant too far down the humerus can result in deltoid lag. Similarly, the offset of the face of the head relative to the stem must be established correctly or excess or insufficient tension in the rotator cuff may be created. Unfortunately, with existing designs there is no way to evaluate implant height or head offset prior to final installation, after which correction is difficult.

SUMMARY OF THE INVENTION

The present invention is a shoulder prosthesis having a head and an elongate stem portion including a proximal end connected to the head, a distal section for insertion into a medullary canal of a humeral bone and an alignment section disposed between the proximal end and distal section. The alignment section includes a plurality of reference marks positioned to facilitate placement of the prosthesis in the bone at a previously determined position.

BRIEF DESCRIPTION OF THE FIGURES

FIG. 3 is a cross-sectional view of a shaft of the implant of FIG. 1.

FIGS. 4–9 are various views of a body portion of the implant of FIG. 1.

FIG. 15 is an isometric view of the head partially installed on the body.

FIG. 16 is a cross-sectional view of the implant along line 8—8 of FIG. 3.

DETAILED DESCRIPTION

Figure 1:
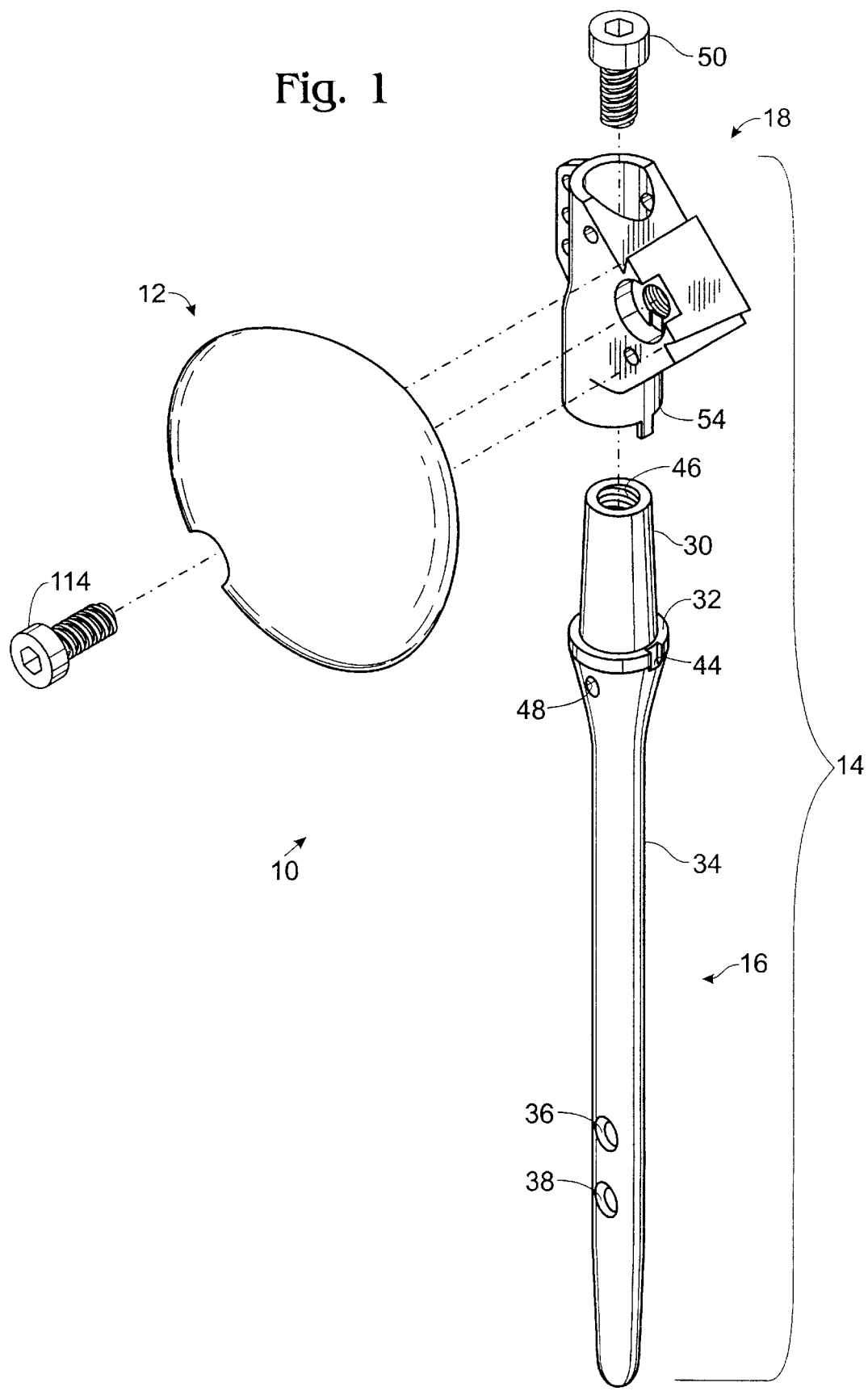
FIG. 1 is an exploded isometric view of a modular shoulder implant constructed according to the present invention.
Figure 2:
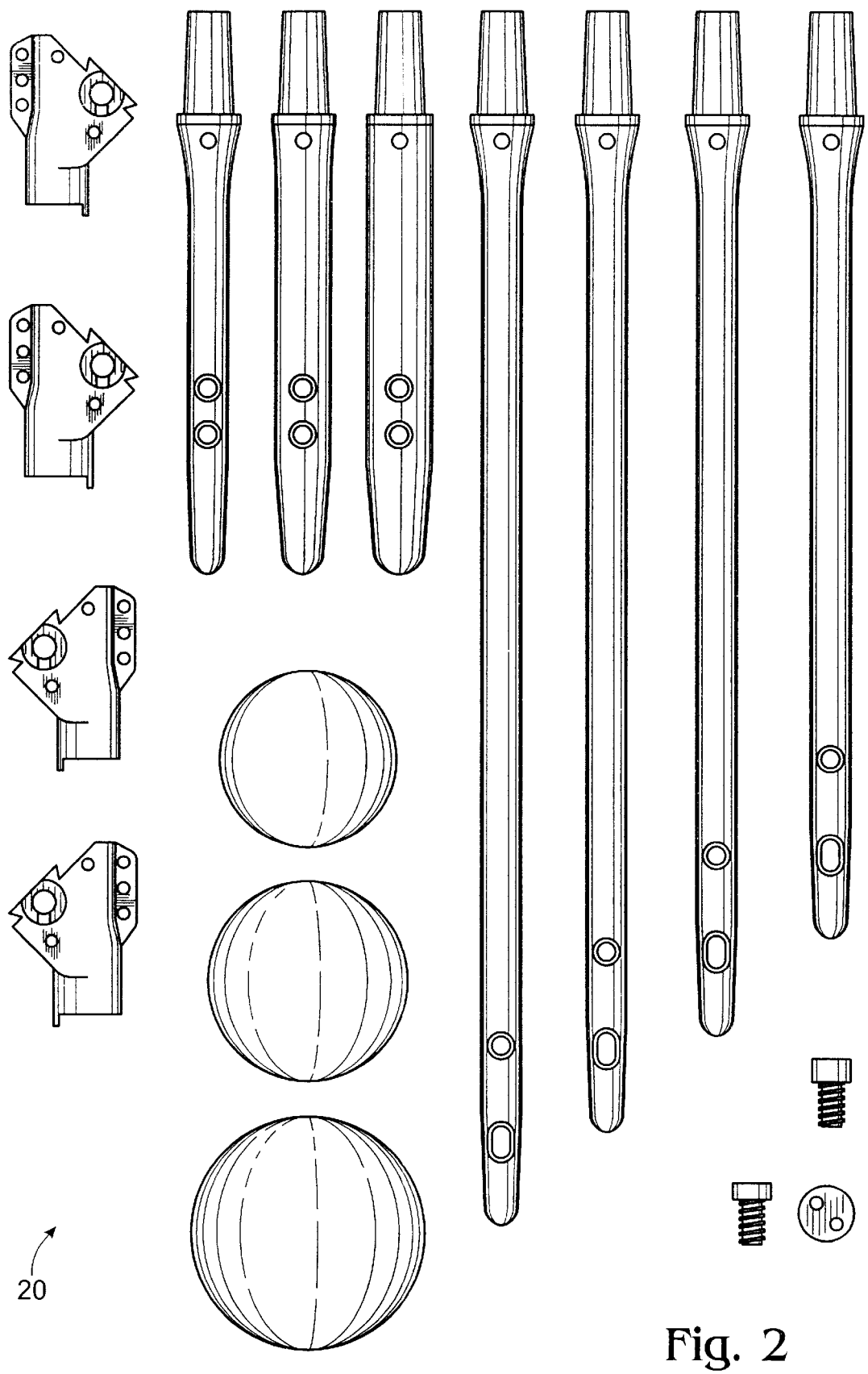
FIG. 2 shows a modular shoulder implant kit constructed according to the present invention.
Figure 10:
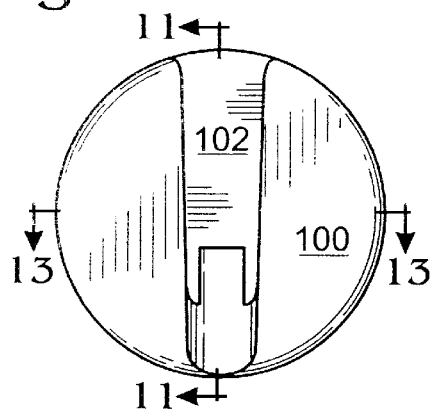
FIGS. 10–13 are various views of a head portion of the implant of FIG. 1.
Figure 11:
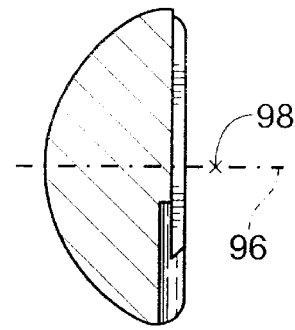
Figure 12:
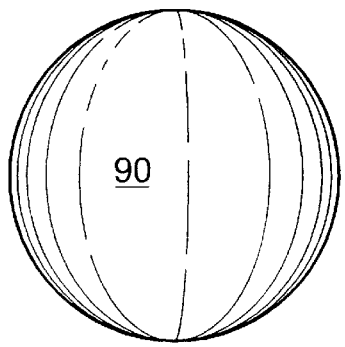
Figure 13:
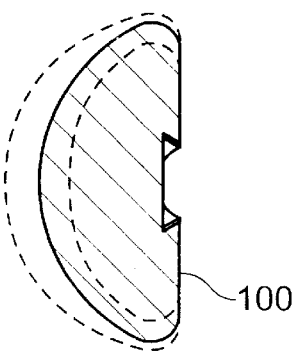

A shoulder implant constructed according to the present invention is shown generally at 10 in FIG. 1. Implant 10 includes a head 12 and a stem 14. The stem preferably includes a distal shaft 16 and a body 18. The components making up implant 10 are preferably chosen from a kit 20 of interchangeable shafts, bodies and heads, as shown in FIG. 2. By selecting an appropriate shaft, body and head from kit 20, a surgeon is able to create an implant that is sized properly for almost any patient. It should be noted that positional references such as anterior/posterior, medial/lateral and proximal/distal used herein are made with reference to an implant as it would be positioned in a patient.

Shaft 16 is shown in greater detail in FIG. 3 and includes a proximal tapered end 30 extending distally to a shoulder 32 which tapers smoothly into a cylindrical medial region 34 with distal locking holes 36, 38. As can be seen in FIG. 2, the shaft can have a medial region of varying diameter and/or varying length. Generally speaking, the longer shafts are used where there is a mid-shaft fracture in addition to the proximal trauma. The varying diameter short shafts are used to accommodate size variations in the proximal end of the humerus. Either or both of holes 36, 38 may be elongated to allow for movement of the medial region over the locking screws. This is normally desirable when the implant is used to treat a combined mid-shaft fracture.

A rounded and tapered distal tip 40 is formed on the end of medial region 34. Shaft 16 preferably includes a central canulation 42 which can be used to guide the implant into the humerus with the aid of a guide wire. As best shown in FIG. 1, an alignment notch 44 is formed in shoulder 32 to aid in establishing the correct orientation of the body on the shaft, as will be described below. A threaded hole 46 is formed in tapered end 30 to receive a screw 50 which is used to draw the body firmly onto the tapered end. A wiring hole 48 is provided just distal of shoulder 32 to allow tension band wiring to be secured through the implant. In addition, when the implant is to be cemented in place, a K-wire can be driven through humerus and hole 48 to fix the position of the implant while the cement cures.

As indicated in FIG. 1, body 18 mounts to the top of shaft 16. Referring to FIGS. 4–9, body 18 has a distal end 54 with a cylindrical tapering socket 56 extending upwardly therefrom into the body. Socket 56 is sized to receive tapered end 30 of shaft 16 and taper-lock thereto to allow the body to be securely mounted to the shaft. A proximal bore 58 extends from the socket to the top of the body to the previously discussed screw to engage the top of the shaft to draw it into the socket. A small rib 60 is provided in the bore to engage against the head of the screw.

Figure 17:
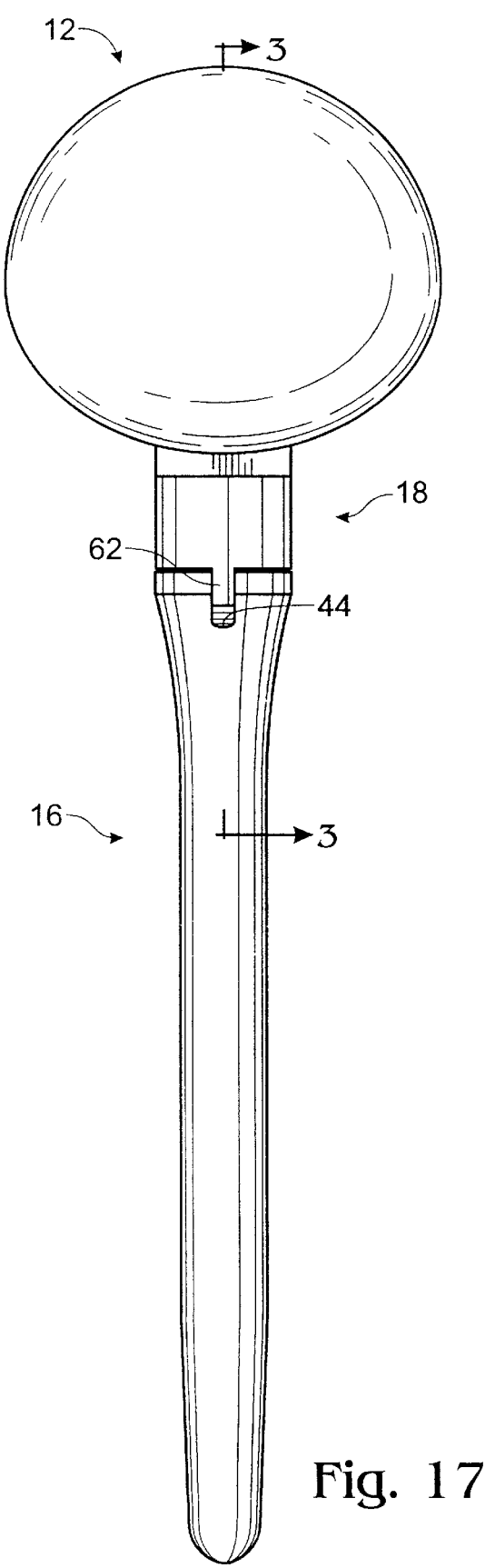
FIG. 17 is a medial elevational view of the implant of FIG. 1.

A small finger 62 projects down from the distal end of body 18 adjacent the socket to engage alignment notch 44 as the body is installed on the shaft. See FIGS. 1 and 17. This ensures the proper rotational positioning of the body on the shaft so that the various holes in the shaft are oriented correctly. Body 18 further includes a lateral rib 64 with three suture holes 66 which aid in securing the fracture fragments to the implant. Upper and lower medial suture holes 68, 70 are also provided in body 18 to offer additional options in securing the fragments. A medially-positioned, anteriorly-oriented threaded hole 72 is formed in body 18 to receive a screw for securing the head to the body. Hole 72 also serves as a mounting point for a targeting/installation instrument used with the implant. A recess 74 is located at the top of the hole and includes a keying notch 76 for orienting the targeting/installation instrument. See Pigs. 1 and 4. The recess allows the screw head to install substantially flush with the surface of the body to minimize the amount of bone removal required to insert the stem into the humerus.

Body 18 includes a medially-facing inclined mounting surface 80 at the proximal end onto which head 12 is mounted. Head 12 is secured to body 18 by coupling structure 82 which includes a fitting in the form of a pedestal or dovetail 84 located on mounting surface 80. As shown in FIGS. 6 and 8, dovetail 84 is tapered from anterior to posterior to establish a taperlock with the head, as will be described below. Because the dovetail is tapered, the body has a left or right orientation depending on which shoulder is to be replaced. Thus, as shown in FIG. 2, the kit will preferably include two or more bodies. Additional bodies, over and above one left and one right, may be provided to accommodate different stem diameters or head angles, etc.

Head 12, which is preferably formed as a unitary member, as opposed to being assembled from two or more components, includes a generally semi-spherical articulation surface 90 which is adapted to engage the glenoid cavity in the shoulder. See FIGS. 10–13. Because the glenoid cavity does not define a close fitting socket such as found in the acetabulum in the hip joint, the articulation surface only needs to be sufficiently spherical to allow smooth articulation in the glenoid cavity.

Figure 14:
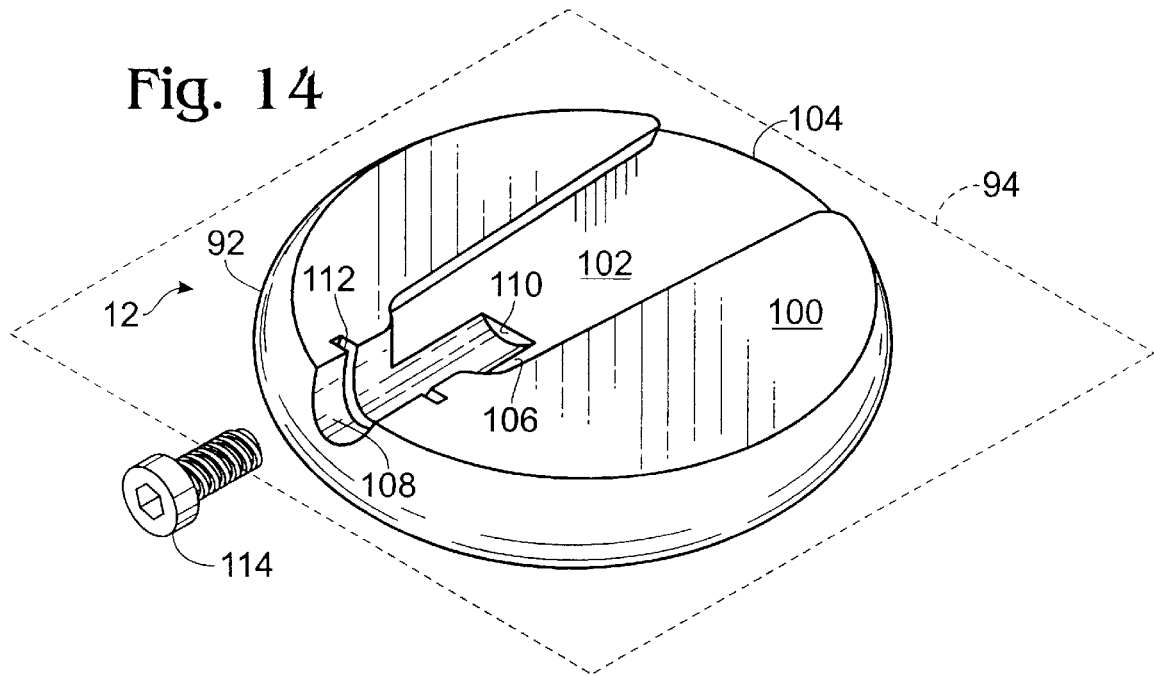
FIG. 14 is an isometric view of the backside of the head of FIGS. 10–13.

As best shown in FIG. 14, articulation surface 90 is bounded by an articular margin 92 which defines an articular plane 94 generally normal to a head axis 96. In the preferred embodiment, where the head is substantially spherical, the head axis represents a central axis of rotational symmetry for the articulation surface and a center of curvature 98 lies on the head axis. See FIG. 11. As shown by the dotted lines in FIG. 13, the various heads are preferably formed with the same radius, but simply represent larger portions of a sphere. It is believed that this best reflects the actual anatomical characteristics.

In the most commonly occurring fracture pattern, the anatomic head fractures generally through the articular margin and plane. The articular plane defines generally the distal extent of head 12. This is important when it is necessary to remove the head as part of a revision procedure, because the present invention allows the head to be removed from an anterior direction without dislocation of the joint and the associated trauma. This is not the case with existing implant heads, which cannot be separated from the body for removal without first dislocating the joint. It is desirable, although not required, that the head not project substantially beyond the articular plane in the present invention so that it is possible to slide the head out of the joint in an anterior direction without disruption of the surrounding bone. Because the remainder of the humerus is distal to the articulation plane, the head may be slid out in that plane without disruption of the surrounding bone as long as the head does not project substantially beyond the articular plane. Thus, the coupling structure is adapted to allow the head to be installed on and removed from the stem without dislocating the shoulder after the implant has been installed in the shoulder.

Head 12 includes a mounting surface or backside 100 disposed opposite the articulation surface and separated from the articulation surface by the articular margin. Backside 100 includes a portion of coupling structure 82 in the form of a transverse track or undercut channel 102. Channel 102 is cut to match the cross-sectional shape and taper of dovetail 84 and includes an open end 104 and an inner end 106. A cylindrical recess 108 extends from the perimeter of the head past the inner end of the channel and to a stop 110. A groove 112 is formed in recess 108 near the edge of the head.

The channel is sized so that the head is guided onto the body and the dovetail taperlocks in the channel when the head is properly positioned. See FIG. 10. The taperlock connection is important because it rigidly secures the components and prevents them from fretting against each other and generating debris over time. The coupling structure of the present invention may also be described as a transversely acting taper lock, with a portion of the taper lock being disposed on the head and a portion disposed on the body. The taper lock of the present invention is transverse acting in that it does not rely on motion along the axis of the head to lock, contrary to existing designs. In fact, it can be seen that, when the head is engaged on the stem, the coupling structure mechanically interlocks the head against motion transverse to the articular plane. This is in contrast to existing designs, which simply rely on a frictional interconnection in the direction transverse to the articular plane.

A locking member in the form of a screw 114 is provided to draw the head firmly onto the body to properly seat the taperlock. In particular, after head 12 is initially positioned on the body, as shown in FIG. 15, it is slid generally into position and screw 114 is installed into hole 72 with the head of the screw fitting closely into cylindrical recess 108. See FIG. 16. As the screw is driven in, the head of the screw engages stop 110 to pull head 12 firmly onto body 18. Screw 114 also serves as a backup interlock to insure that the head does not become dislodged. It should be noted that the head of the screw will not seat completely against the body because some space must be left to accommodate machining tolerances in the coupling structure so that the taper lock may be drawn tight in all cases.

When it is necessary to remove the head, as in a revision, a tool 120 with a flange 122 secured near the tip of the tool is utilized. See FIG. 16. The tip of the tool is initially installed in the screw head from a slight angle away from the head and then the tool is rotated toward the head to engage the flange with taper breaking surface in the form of a groove 112 formed in recess 108. As the screw is backed out, the flange pulls against the head to dislodge the taperlock. Thus, the head can be removed with application of external force to the implant, as has been required with prior designs. This reduces the chance that the entire implant will be loosened when only the head needs to be removed.

Figure 18:
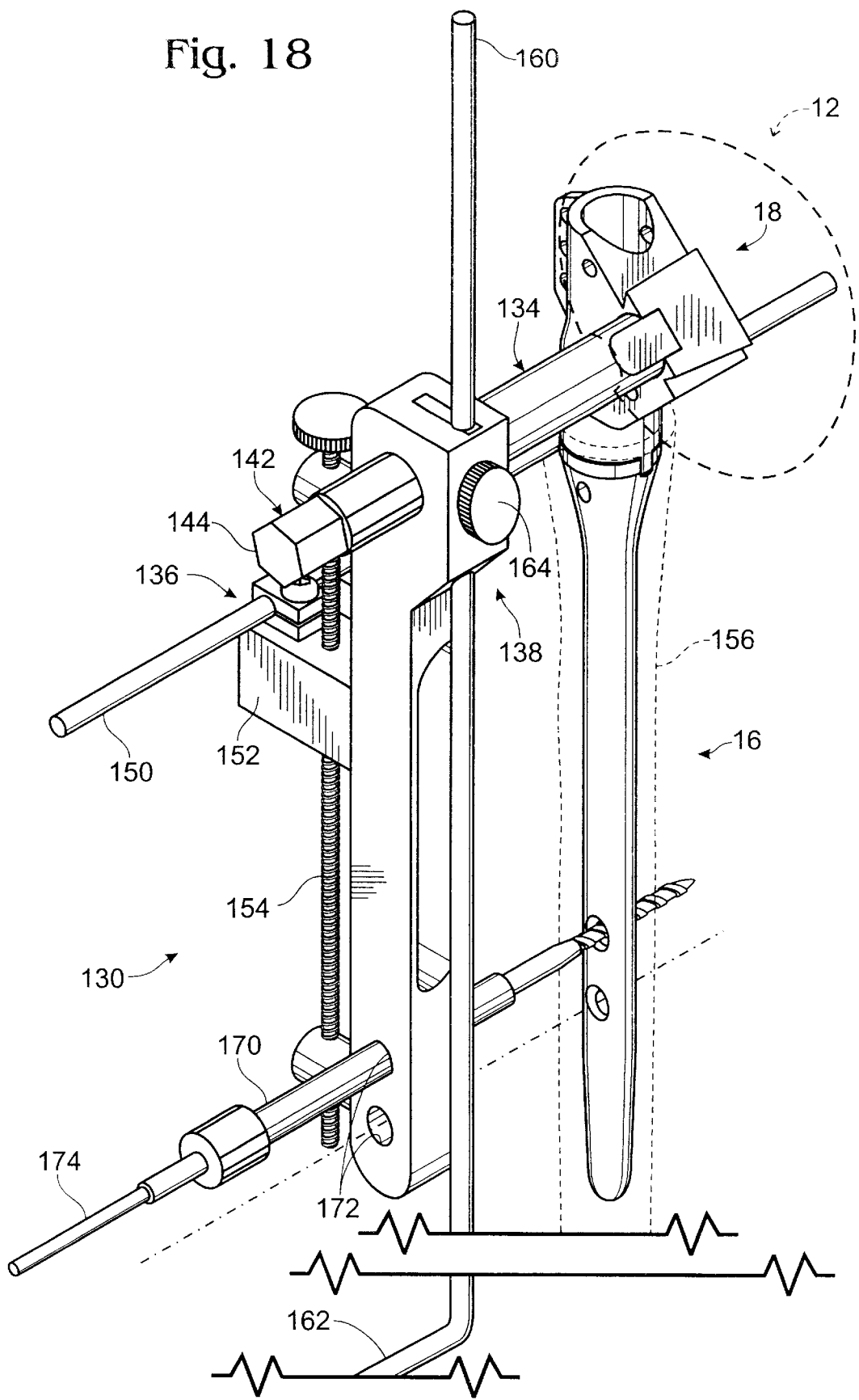
FIG. 18 is an isometric view of a targeting/installation instrument according to the present invention.

Installation of the implant of the present invention is facilitated by a targeting/installation instrument, shown generally at 130 in FIG. 18. Instrument 130 includes a template member 132 to which are mounted a mounting bar 134, a height adjusting mechanism 136 and a retroversion guide 138. Mounting bar 134 serves to join template member 132 to implant 10. In particular, bar 134 is hollow and includes a tab 140 (not shown) at the free end. The bar receives a bolt 142 with a head 144 and a threaded end 146. To attach the instrument to the implant, the free end of the bar is placed in recess 74 and aligned so that tab 140 fits into keying notch 76. This establishes the correct alignment between the template and the implant. The threaded end of the bolt is then screwed into hole 72 to secure the instrument to the implant. The bar includes a flat 148 to allow the bar to reach body 18 without engaging head 12. In addition, it should be noted that the screw which secures the head to the body is not installed until after the instrument is removed.

Once the instrument is mounted to the implant, the stem is inserted into the shaft of the humerus. In the typical fracture pattern, the head and greater and lesser tubercles are separated from the remainder of the humerus, leaving a pipe-like upper shaft. As a result, there is no remaining reference for the correct height of the implant head relative to the top of the humeral shaft. It is important to position the head at the correct height relative to the humeral shaft to avoid excess tension on the deltoid muscle by having the head too high or deltoid lag where the head is too low and the deltoid must undergo some contraction prior to starting to move the arm.

Figure 19:
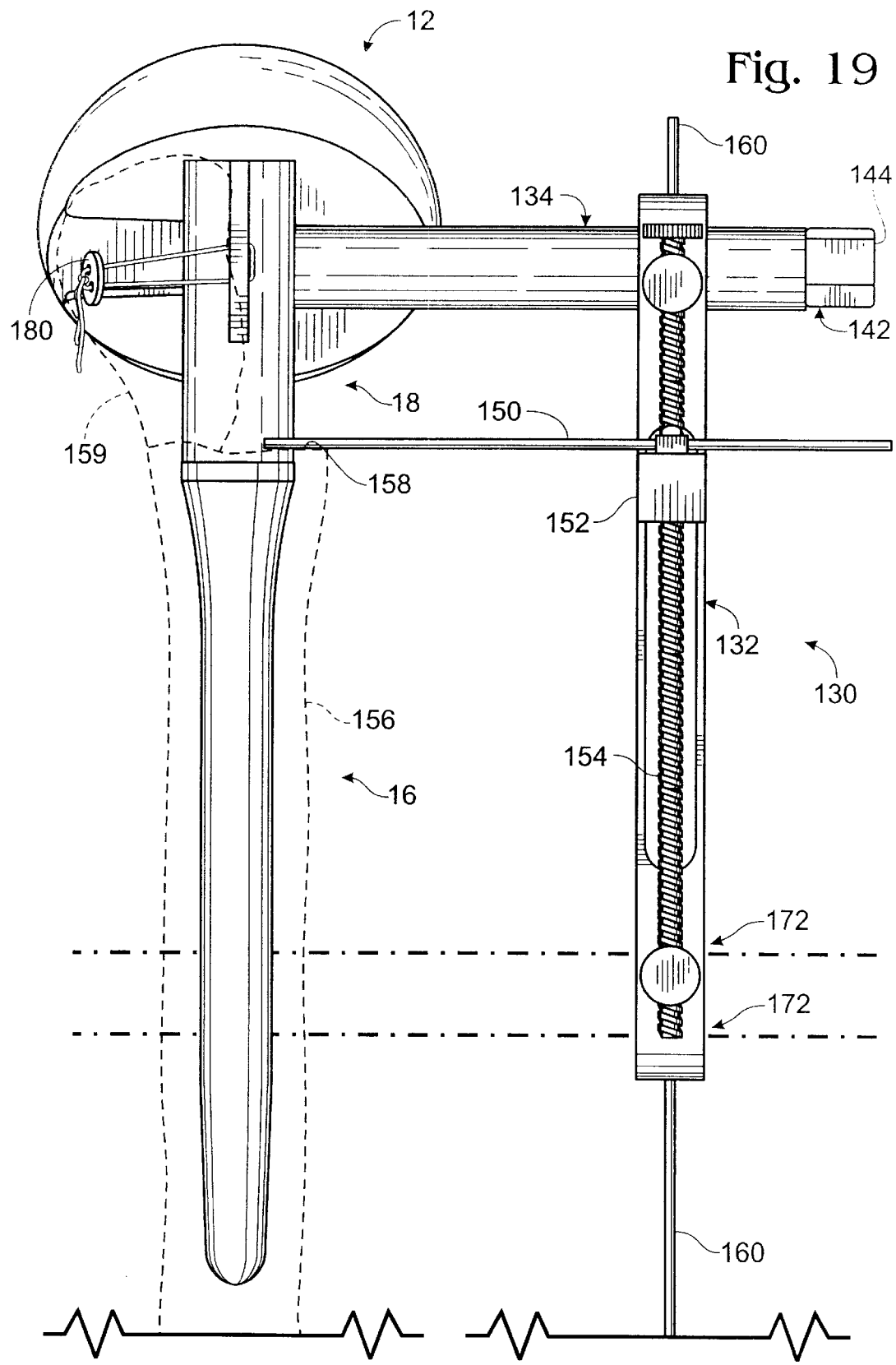
FIG. 19 is a lateral elevational view of the targeting/installation instrument of FIG. 10.

The height adjusting mechanism allows the surgeon to temporarily set the height of the head and then evaluate the deltoid tension. In particular, as shown in FIGS. 18 and 19, height adjusting mechanism 136 includes a guide bar 150 which is moveably mounted to a carriage 152, which is driven up and down along a threaded rod 154. With the implant in a humeral shaft 156, the guide bar is positioned to sit on top 158 of the humeral shaft. The surgeon can then adjust the implant up or down by turning the threaded rod. The guide bar establishes a predetermined height, which can be maintained while retroversion is set and even if the implant is removed and reinserted, as when bone cement is used.

Figure 20:
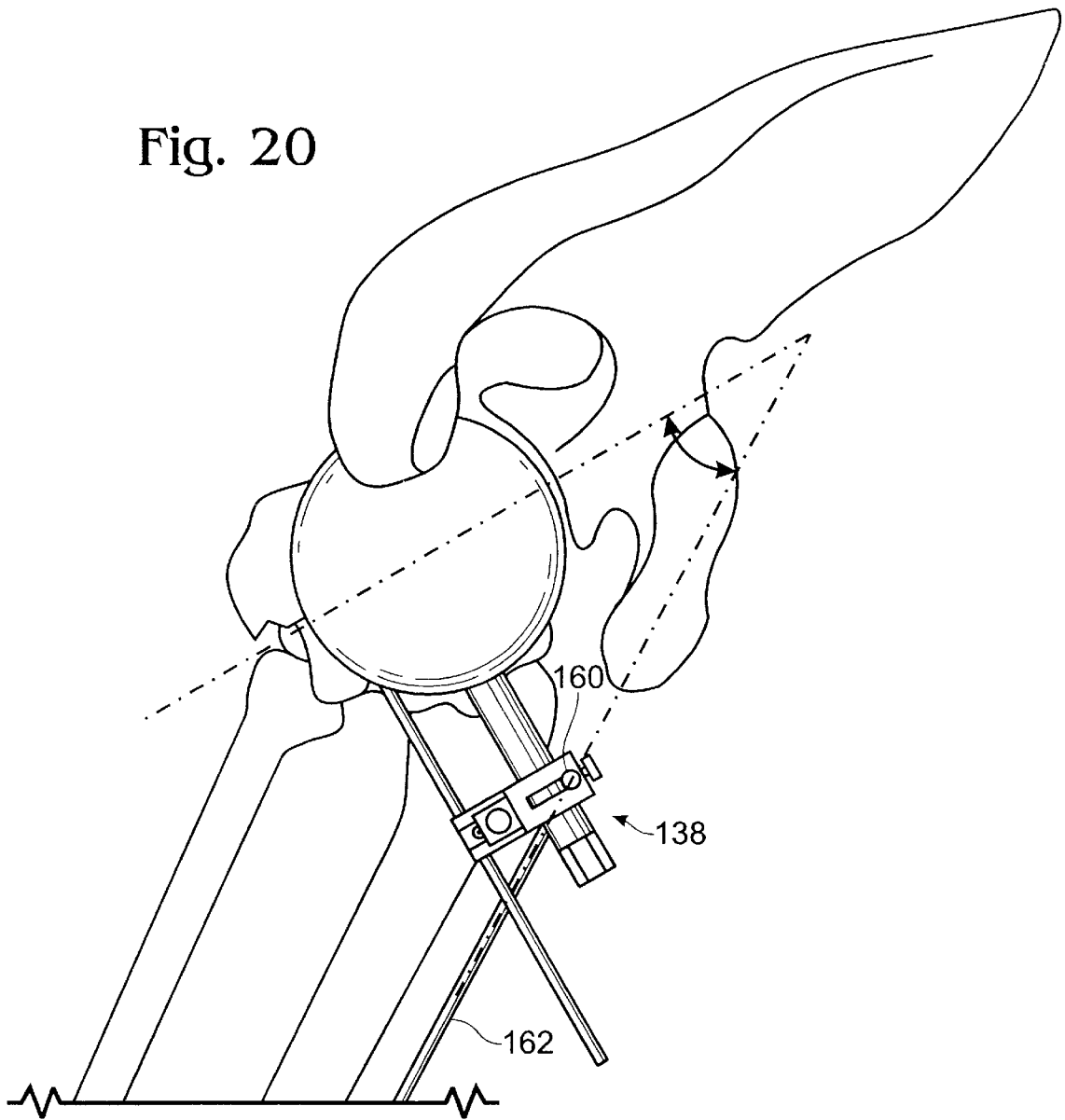
FIG. 20 is an elevational view from above of the targeting installation instrument of FIG. 18.

After establishing the correct height the surgeon can use the retroversion guide to set correct retroversion, as shown in FIG. 20. The retroversion guide includes an L-shaped rod 160 with a lower sighting arm 162. Rod 160 is pivotally and slidably mounted to template 132 to allow the height and angular orientation of the sighting arm to be adjusted. A set screw 164 allows the position of the rod to be fixed once it is in the desired orientation. In use, the sighting arm is set for a predetermined retroversion angle relative to the head axis, for instance 30-degrees. This can be accomplished before attachment to the implant using a protractor jig (not shown). With the sighting arm set to the correct orientation, the patient's forearm is flexed to approximately 90-degrees to the humerus. The surgeon then rotates the implant to align the sight arm with the axis of the forearm, thereby easily and accurately establishing the desired retroversion.

Once the correct height and retroversion is established, a cannulated drill guide 170 is inserted through guide holes 172 provided in the distal end of the template member. See FIG. 18. Guide holes 172 are oriented to target locking holes 36 in the end of the stem. A drill 174 is inserted though the drill guide to bore through the bone over the locking holes. One or two screws are installed through the humerus and locking holes to secure the implant in place.

Figure 21:
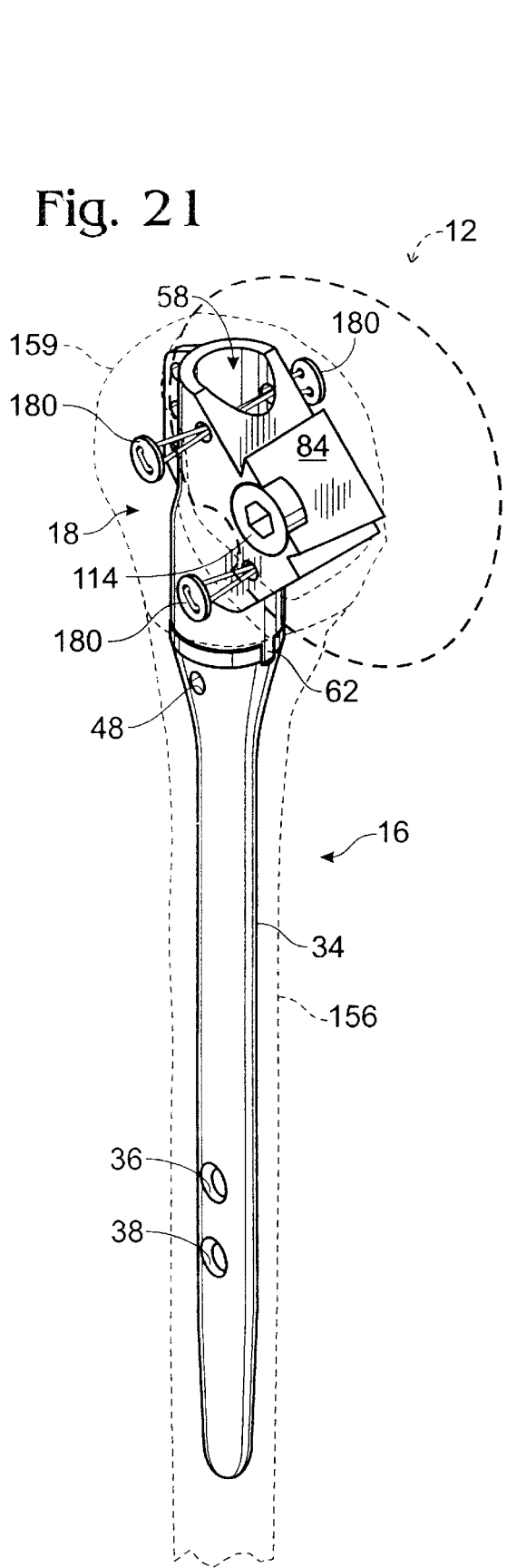
FIG. 21 is an isometric view of the implant of FIG. 1 in an assembled configuration.

As shown by the dotted lines in FIG. 19, it is possible to attach the greater tubercle 159 to the implant prior to final securing of the head. This allows the surgeon to evaluate the tension in the rotator cuff and make corrections, if necessary, by moving to a smaller or larger head. One other feature of the present invention is the provision of suture supports 180, shown in FIG. 21, which serve to distribute the force of the suture over the bone. Particularly in trauma cases, the bone is very soft and without supports 180, the sutures will sometimes pull through the bone. By utilizing the supports, the surgeon can obtain the desired suture tension without risk of the suture pulling through the surface of the bone.

It should be noted that the targeting/installation instrument is provided in left and right versions, although it would also be possible to make mounting bar 134 reversible or symmetric to accommodate left and right bodies. In addition, a longer template member would be used with the longer shafts used to treat mid-shaft fractures.

Figure 22:
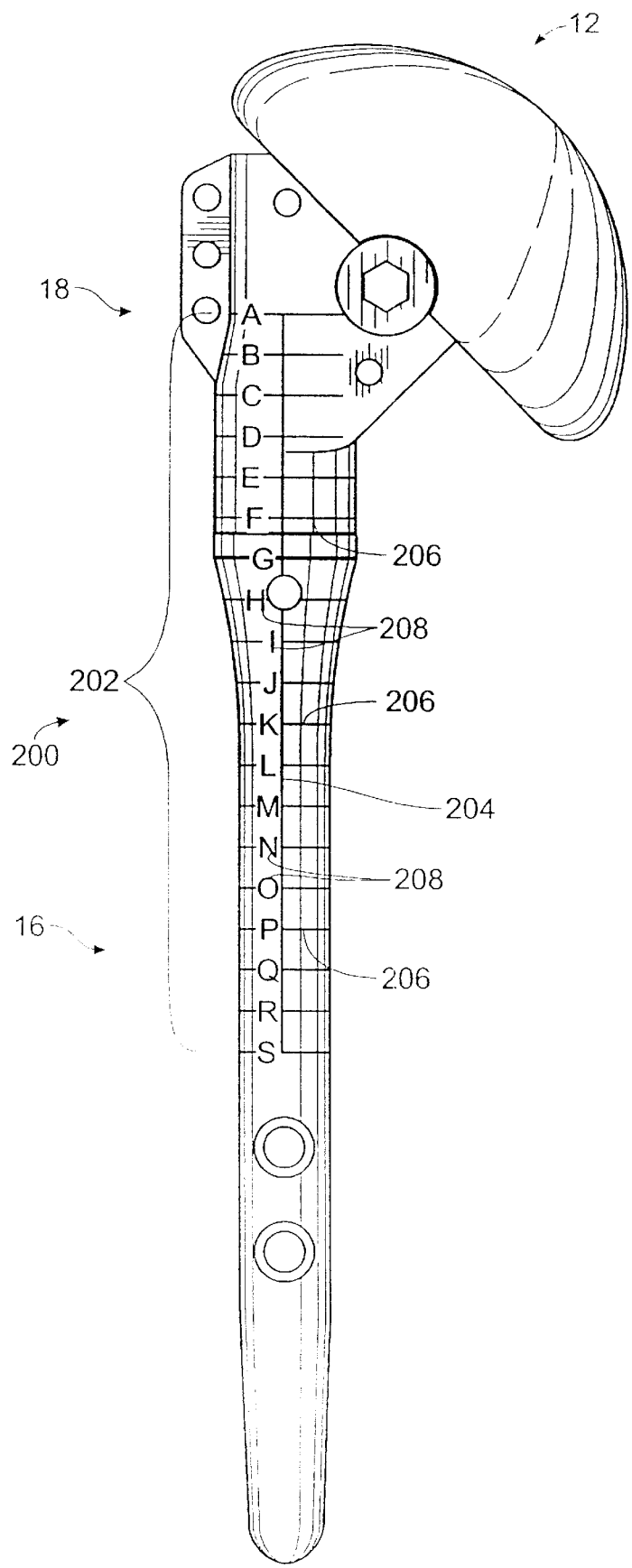
FIG. 22 is a side elevational view of an implant showing reference marks.

Installation and alignment of the implant can also be facilitated by placing indications or reference marks on the implant as shown at 200 in FIG. 22. Reference marks 200 are placed in an alignment section 202 of the stem, generally in the area of the stem which will lie adjacent the top of the humeral shaft when installed. Preferably, the reference marks include one or more angular marks such as angular indication 204 and multiple vertically-spaced gradations 206, allowing both height and angular orientation to be monitored. A plurality of indicia such as letters 208 are applied to the vertically-spaced gradations marks at intervals to make identifying a particular gradation easier. The marks can be laser marked on the surface of the implant, etched into the implant or applied via any other standard marking process. It should be noted that the marks and indicia would normally be viewed from the anterior direction and are therefore preferably placed on that side. In the case of implants that can be placed on either the left or right side, the marks and indicia would preferably be formed on both sides of the implant so that they were visible in either case.

In use, the surgeon first installs one or more trial prostheses to obtain proper fit and positioning in the fashion described above. The trial prostheses are typically identical to the actual prosthesis, but are assembled from a kit of components that are reused from operation to operation. The trial prostheses are equipped with reference marks at the same locations as the actual prosthesis. Once the correct fit and positioning are established, the surgeon notes which gradation is positioned adjacent to the top of the humeral shaft. The surgeon then marks the bone with a methylene blue dye marker at the top of the shaft in line with the angular indication. The surgeon can then take the actual implant and place it in the bone and replicate the trial position, which includes an angular orientation and a depth component, by aligning the previously-noted marks on the actual implant with the previously-determined location on the bone.

It should be understood that the alignment marks could be implemented on a modular or unitary implant and could be used alone or in conjunction with the above-described targeting instrument. Moreover, such marks are beneficial, even when used without a trial device, to verify that an implant has not moved after the desired position has been established.

Figure 23:
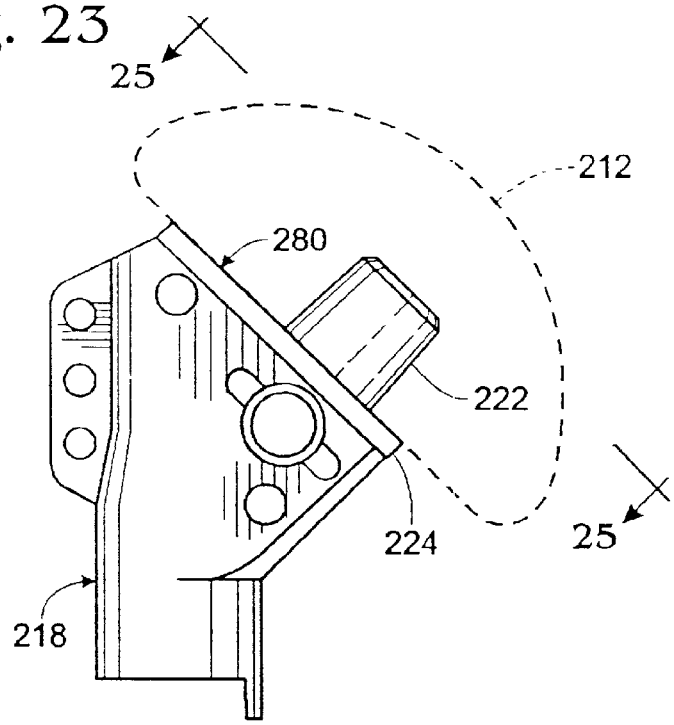
FIG. 23 is a side elevational view of a body constructed according to the present invention.

Another embodiment of a body for use with a shoulder implant according to the present invention is shown at 218 in FIG. 23. Body 218 is similar in construction to body 18, but includes a tapered stud 222 formed on an upper mounting surface 280. A head 212 is adapted to be mounted to body 218 by mounting on stud 222. More specifically, the head includes a tapered bore 226 which fits over stud 222 and is sized to form a taper lock therewith, thus securing the head to the body. A collar 224 forms the lower boundary of mounting surface 280. See FIG. 24. The collar serves to prevent the body from subsiding down into the humerus and creating an outward pressure on the head tending to loosen the taper lock.

Figure 25:
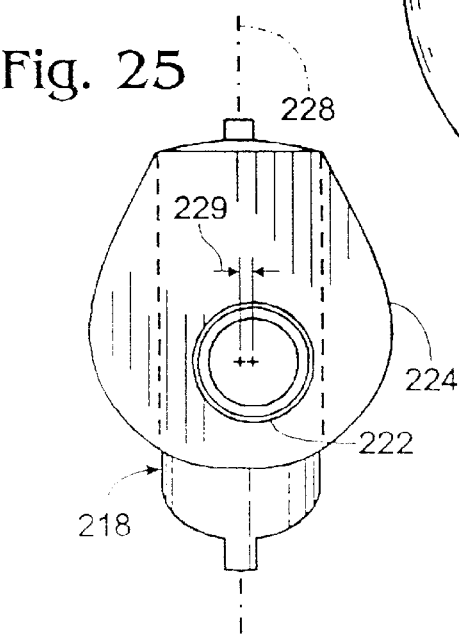
FIG. 25 is an elevational view along line 25—25 in FIG. 23.

As best seen in FIG. 25, the axis of the tapered stud is offset from an anterior/posterior plane 228 of the body and stem. In the disclosed embodiment, the offset, indicated at 229, is approximately two millimeters in the posterior direction, as implanted. Generally, suitable offset could be between approximately 1 and 5 millimeters. As a result of the offset, the bodies are provided in left and right versions which are mirror images of each other.

Figure 24:
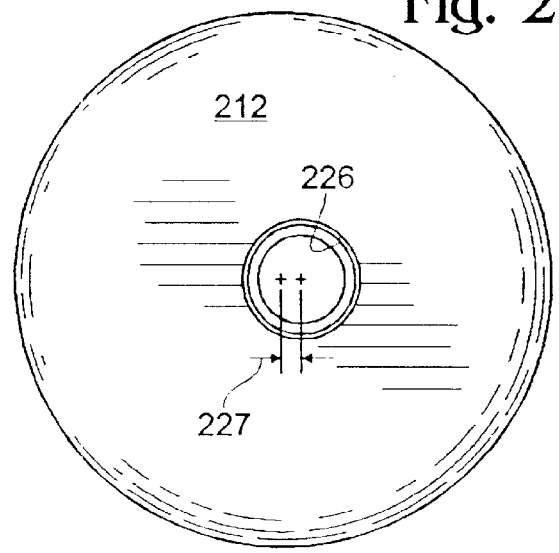
FIG. 24 is an elevational view of the rear surface of a head constructed according to the present invention.

In the disclosed embodiment, the tapered bore is positioned approximately 1 millimeter offset from the center of the head as depicted at 227 in FIG. 24. This offset allows the surgeon to rotate the head to achieve any desired offset between 1 and 3 millimeters. By offsetting the tapered stud from the anterior/posterior plane, the surgeon is able to achieve a range of posterior offsets without introducing excessive superior/inferior offsets. Although the head is shown with an offset, it is possible that the head might not have any offset, thus eliminating any superior/inferior offset. One of the benefits of eliminating head offset is that it is possible to introduce the desired anterior/posterior offset via the body without introducing other perturbations into the positioning of the head. It is generally desirable to keep the head offset to a minimum to reduce the torque created by the offset.

In addition to providing the body in left and right versions, it may be desirable to provide multiple left and right bodies with various offsets. Because heads are substantially more costly to produce than bodies, providing multiple bodies offers a more economical approach to achieving a wide variety of anatomical offsets. The body can be manufactured by machining from bar stock or may be cast. Another benefit of providing side-specific bodies is that the size of the body can be kept to a minimum in comparison to adjustable bodies. Minimizing the size of the body reduces the amount of bone that must be removed to install the implant, It should be noted that the anterior/posterior offset described in the context of a cylindrical taper lock could also be implemented on the dovetail taper lock previously described by simply offsetting the taper lock in the head or on the body or both.

While the invention has been disclosed in its preferred form, the specific embodiments thereof as disclosed and illustrated herein are not to be considered in a limiting sense as numerous variations are possible. Applicant regards the subject matter of his invention to include all novel and non-obvious combinations and subcombinations of the various elements, features, functions and/or properties disclosed herein. No single feature, function, element or property of the disclosed embodiments is essential. The following claims define certain combinations and subcombinations which are regarded as novel and non-obvious. Other combinations and subcombinations of features, functions, elements and/or properties may be claimed through amendment of the present claims or presentation of new claims in this or a related application. Such claims, whether they are broader, narrower or equal in scope to the original claims, are also regarded as included within the subject matter of applicant's invention.

I claim:

1. Apparatus for repairing a fractured humeral bone comprising:
   a shoulder prosthesis having a shaft positionable within the medullary canal of a humeral bone; and
   a positioning jig for positioning the shoulder prosthesis at a desired height in the medullary canal, wherein the positioning jig includes
      a first member positionable adjacent the humeral bone,
      a second member coupled to the first member and configured to engage an exposed portion of the humeral bone to support the first member adjacent the humeral bone, and
      a third member coupled to the first member and configured to engage the shoulder prosthesis and hold the shoulder prosthesis at the desired height in relation to the exposed portion of the humeral bone.

2. The apparatus of claim 1, wherein the second and third members are spaced apart along the first member.

3. The apparatus of claim 2, wherein the spacing between the second and third members is adjustable to allow the height of the shoulder prosthesis to be adjusted in relation to the exposed portion of the humeral bone.

4. The apparatus of claim 1, wherein the positioning jig includes an alignment rod coupled to the third member at a predetermined angle relative to the shoulder prosthesis to allow the shoulder prosthesis to be positioned with a desired retroversion in the humeral bone.

5. The apparatus of claim 4, wherein the third member is configured to engage the shoulder prosthesis to prevent relative rotation between the shoulder prosthesis and the positioning jig.

6. The apparatus of claim 4, wherein the shoulder prosthesis includes one or more angular reference marks to facilitate positioning of the shoulder prosthesis with the desired retroversion.

7. The apparatus of claim 1, wherein the shoulder prosthesis includes a plurality of vertically spaced markings to facilitate positioning of the shoulder prosthesis at the desired height.

8. The apparatus of claim 1, wherein the positioning jig is configured to target one or more locations on the humeral bone corresponding to one or more holes on the prosthesis shaft.

9. Apparatus for repairing a fractured humeral bone comprising:
   a shoulder prosthesis; and
   a positioning jig for positioning the shoulder prosthesis at a desired height in the medullary canal of the humeral bone, wherein the positioning jig includes
      a first mechanism configured to engage an upper portion of the humeral bone, and
      a second mechanism coupled to the first mechanism and configured to engage and hold the shoulder prosthesis at the desired height relative to the upper portion of the humeral bone.

10. The apparatus of claim 9, wherein the second mechanism is movably coupled to the first mechanism to allow the height of the shoulder prosthesis to be adjusted relative to the upper portion of the humeral bone.

11. The apparatus of claim 9, wherein the second mechanism is slidably coupled to the first mechanism.

12. Apparatus for repairing a fractured humeral bone comprising:
   a shoulder prosthesis; and
   a positioning jig for positioning the shoulder prosthesis with a desired retroversion in the medullary canal of the humeral bone, wherein the positioning jig includes
      a mounting mechanism configured to removably attach to the shoulder prosthesis; and
      an alignment rod coupled to extend from the mounting mechanism at a predetermined retroversion angle relative to the shoulder prosthesis such that when the alignment rod is aligned relative to a patient's flexed forearm, the shoulder prosthesis is positioned with the predetermined retroversion in the humeral bone.

13. The apparatus of claim 12, wherein the alignment rod is coupled to extend from the mounting mechanism at a predetermined retroversion angle of 30-degrees relative to the shoulder prosthesis.

14. The apparatus of claim 12, wherein the alignment rod is adjustable to change the retroversion angle.

15. The apparatus of claim 12, wherein at least a portion of the alignment rod extends proximate the patient's flexed forearm.

16. The apparatus of claim 12, wherein the shoulder prosthesis includes one or more angular reference marks to facilitate positioning of the shoulder prosthesis with the desired retroversion.

* * * * *